United States Patent [19]

Garren et al.

[11] 4,416,267
[45] Nov. 22, 1983

[54] METHOD AND APPARATUS FOR TREATING OBESITY

[76] Inventors: Lloyd R. Garren; Mary L. Garren, both of P.O. Box 3738, Wilmington, Del. 19807

[21] Appl. No.: 329,182

[22] Filed: Dec. 10, 1981

[51] Int. Cl.³ .............................................. A61B 17/00
[52] U.S. Cl. .................................... 128/1 R; 128/344; 128/303 R; 604/96; 604/103
[58] Field of Search ............... 128/1 R, 344, 346, 325, 128/129, 303 R; 604/93, 96–97, 101–103

[56] References Cited

U.S. PATENT DOCUMENTS

| | | | |
|---|---|---|---|
| 4,085,757 | 4/1978 | Pevsner | 604/96 X |
| 4,102,342 | 7/1978 | Akiyama et al. | 128/325 |
| 4,133,315 | 1/1979 | Berman et al. | 604/96 X |
| 4,134,405 | 1/1979 | Smit | 128/303 R |
| 4,246,893 | 1/1981 | Berson | 128/346 X |
| 4,311,146 | 1/1982 | Wonder | 128/344 X |
| 4,315,509 | 2/1982 | Smit | 128/303 R |

FOREIGN PATENT DOCUMENTS

WO80/00007  1/1980  PCT Int'l Appl. ................. 128/344

*Primary Examiner*—Lee S. Cohen
*Assistant Examiner*—Angela D. Sykes
*Attorney, Agent, or Firm*—Connolly and Hutz

[57] ABSTRACT

A stomach insert for treating obesity in humans by reducing the stomach volume comprises a flexible torus-shaped inflatable balloon having a central opening extending therethrough. At least a portion of the balloon has a self-sealing substance to facilitate puncture thereof with a needle for inflating the balloon and sealing of the puncture upon removal of the needle. The method herein comprises positioning the balloon inside the stomach of the person being treated for obesity so as to reduce the stomach volume.

7 Claims, 6 Drawing Figures

U.S. Patent        Nov. 22, 1983        4,416,267
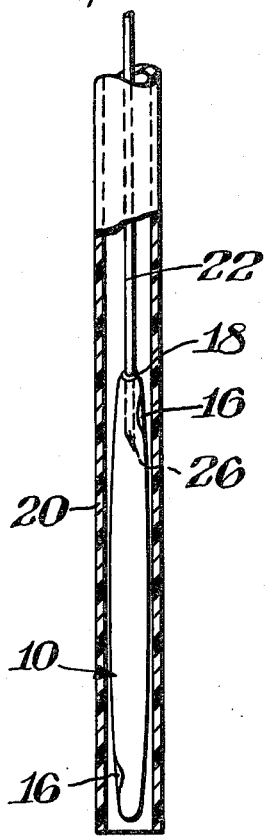
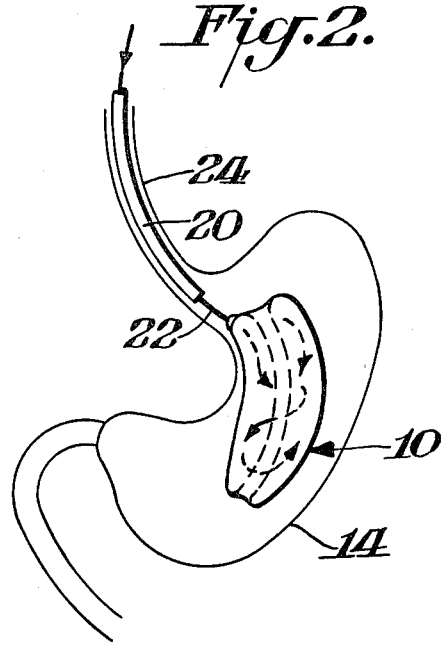
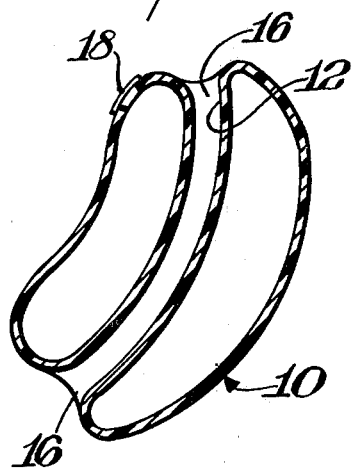
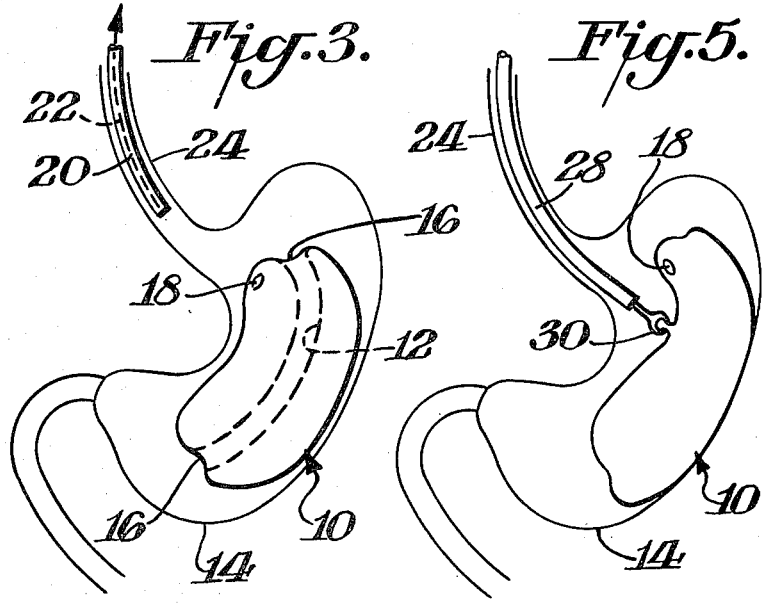
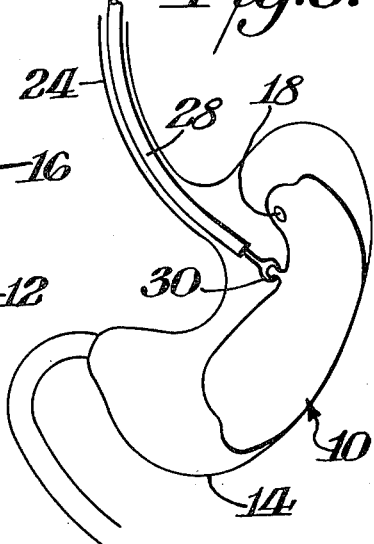
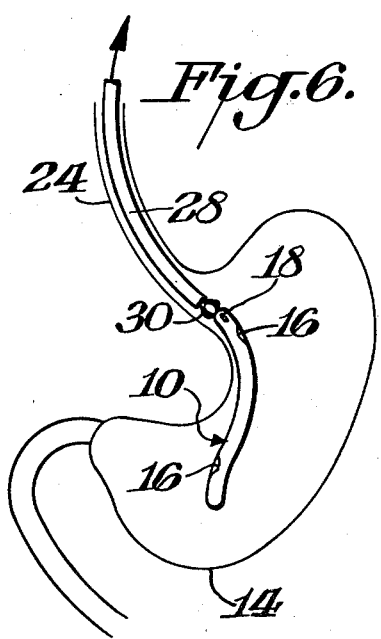

METHOD AND APPARATUS FOR TREATING OBESITY

BACKGROUND OF THE INVENTION

The present invention relates to the medical treatment of obesity in humans, and more particularly to apparatus and methods for curbing the appetite of persons being treated for obesity.

Extreme obesity is a major illness in the United States and other countries. Its complications include hypertension, diabetes, coronary artery disease, stroke, congestive heart failure, venous disease, multiple orthopedic problems and pulmonary insufficiency with markedly decreased life expectancy. Medical management including dietary, psychotherapy, medications and behavioral modification techniques have yielded extremely poor results in multiple trials. Several surgical techniques have been tried which have bypassed the absorptive surface of the small intestine or have been aimed at reducing the stomach size by either partition or bypass. These procedures have been proven both hazardous to perform in morbidly obese patients and have been fraught with numerous life-threatening postoperative complications. Moreover such operative procedures are often difficult to reverse.

Non-surgical approaches for the treatment of obesity include voluntary dieting which is often unsuccessful since most persons do not possess sufficient willpower to limit the intake of food. Other approaches include the use of stomach fillers such as methyl cellulose, often taken in the form of tablets. The methyl cellulose expands in the stomach leaving the person with a filled-up feeling. Also, inflatable bag and tube combinations have been proposed wherein the bag is swallowed into the stomach and the tube attached thereto is used to periodically inflate the bag, particulary just prior to mealtime or during the meal. Once the person has eaten, the bag can be deflated all at once, or it can be deflated gradually over a period of a few hours so as to simulate the condition of digestion occurring and the gradual reduction of stomach contents.

U.S. Pat. No. 4,133,315 granted Jan. 9, 1979 discloses such an inflatable bag and tube combination. The tubing remains attached to the bag and inside the esophagus of the person being treated. These tubes are often the cause of erosions and ulcerations of the esophagus. This patent also discloses a gastrotomy method wherein the permanently attached tube used to distend the stomach bag extends through an opening in the stomach wall as well as an opening in the abdomen.

Also, U.S. Pat. No. 4,246,893 granted Jan. 27, 1981 discloses an inflatable bag and tube combination which is surgically positioned outside and adjacent to the stomach. Upon inflation of the bag the upper abdomen is distended and the stomach compressed to thereby produce a sense of satiety which reduces the persons's desire to ingest food.

Hence, reducing the size of the gastric compartment has been shown to induce weight loss in a significant percentage of people, and the present invention is aimed at a device which nonoperatively reduces the size of the gastric compartment and which is easily removed.

SUMMARY OF THE INVENTION

Accordingly, it is an object of the present invention to treat obesity by curbing a person's appetite in a manner which is safe, convenient and effective.

Another object of the present invention is to treat obesity by effectively reducing the stomach volume of the person being treated.

In accordance with the present invention, a stomach insert for treating obesity in humans by reducing the stomach volume comprises a flexible torus-shaped inflatable balloon having a central opening extending therethrough. At least a portion of the balloon has a self-sealing substance to facilitate puncture thereof with a needle for inflating the balloon and sealing of the puncture upon removal of the needle.

Preferably, the stomach balloon has an inflated volume of approximately 200 to 800 cc. and the central opening thereof includes flared outer ends.

The method for treating obesity in humans according to the present invention comprises the steps of assembling a deflated stomach balloon with an insufflation tube releasably attached thereto inside a standard stomach tube. Thereafter the stomach tube is introduced through the mouth and into the stomach, and the balloon is urged out of the stomach tube into the stomach compartment. The attached insufflation tube is then used to inflate the balloon with air or other fluids. Finally, the insufflation tube is detached from the inflated balloon and along with the stomach tube removed from the body of the person. Usually the balloon is inflated to a volume approximately 80% of the stomach volume.

BRIEF DESCRIPTION OF THE DRAWINGS

Novel features and advantages of the present invention in addition to those mentioned above will become apparent to those skilled in the art from a reading of the detailed invention in conjunction with the accompanying drawings wherein similar reference characters refer to similar parts and in which:

FIG. 1 is a side elevational view of a stomach tube according to the present invention partially broken away to show details of the deflated balloon and its insufflation tube;

FIG. 2 is a schematic side elevational view illustrating the balloon outside the stomach tube and partially inflated inside the stomach;

FIG. 3 is a schematic side elevational view of the balloon fully inflated inside the stomach with the insufflation tube detached from the balloon and both tubes being withdrawn from the person;

FIG. 4 is a cross-sectional side elevational view of the fully inflated balloon shown in FIG. 3;

FIG. 5 is a schematic side elevational view of a fiber-optic gastroscope with needle biopsy forceps extending therefrom in the process of puncturing and removing the balloon from the stomach; and FIG. 6 is a schematic side elevational view similar to FIG. 5 with the balloon fully deflated and ready for removal.

DETAILED DESCRIPTION OF THE INVENTION

Referring in more particularity to the drawings, the several figures herein illustrate a stomach implant or insert for treating obesity in humans by reducing the stomach volume. Specifically, the stomach insert comprises a flexible torus-shaped inflatable balloon 10 having a central opening 12 extending therethrough. The balloon may be fabricated from medical grade rubber or synthetic rubber-like material, one criteria being that such material be impervious so that the balloon is capable of holding a charge of air or other fluid.

As explained more fully below, the central opening 12 provides a passageway for solids and liquids as they pass through the stomach cavity 14. As shown best in FIG. 4, the central opening 12 includes flared outer ends 16 that function to provide wide entrances to the central opening.

Continuing, the balloon 10 includes an injection site 18 fabricated from any self-sealing substance such as used in the injection site of standard intravenous tubing. The injection site 18 serves as a location for inflation of the balloon 10, and the balloon is sized so that its inflated volume is approximately 200 to 800 cc.

A standard levine or stomach tube 20 is utilized to position the balloon 10 inside the stomach. Also, prior to positioning the balloon inside the stomach, an insufflation tube 22 in the form of small bore polyethylene tubing is attached to the deflated balloon. In this regard the free end of the insufflation tube carries a needle 24 which punctures the balloon in the injection site 18. As shown best in FIG. 1, the deflated stomach balloon 10 with the insufflation tube 22 attached thereto are stored inside the stomach tube 20 just prior to introducing the stomach tube through the mouth and into the stomach of the person being treated for obesity. The procedure is as follows.

Once the components are assembled as shown in FIG. 1, the stomach tube is fed through the mouth and esophagus 24 into the stomach cavity 14. Next, the insufflation tube 22 is urged inwardly relative to the stomach tube 20 to thereby position the deflated balloon 10 inside the stomach. Air or another fluid is then introduced into the balloon 10 via the insufflation tube 22, as shown in FIG. 2. After the balloon is inflated to approximately 80% of the stomach volume, the needle end 26 of the insufflation tube is removed from the injection site 18 which self seals after such removal. The needle 26 is then housed inside the stomach tube and the stomach tube then withdrawn from the body of the person leaving a free-floating and unattached inflated balloon.

The inflated balloon is positioned as shown in FIG. 3 with the central opening therein serving as a passageway through the stomach for both liquids and solids. Also, liquid and solid foods pass around the exterior surface of the balloon between that surface and the interior of the stomach wall. As noted above, the balloon is inflated to a volume of approximately 80% of the stomach volume and this phase of the procedure may be accomplished with the aid of x-ray examination, for example. The balloon remains in the stomach for the period the person is being treated for obesity, perhaps a period of three months or more, and it functions to reduce the volume size of the stomach and thereby curb the appetite of the person being treated for obesity.

Upon completion of the treatment, the balloon is easily removed from the stomach by means of a fiberoptic gastroscope 28 with needle biopsy forceps 30. As shown in FIG. 5, the needle biopsy forceps grasp and puncture the balloon 10, and once the balloon is fully deflated it is simply drawn out of the stomach into the esophagus and out through the mouth of the person being treated.

What is claimed:

1. A stomach insert for treating obesity in humans by reducing the stomach volume comprising a flexible, free-floating and unattached, inflatable balloon having a central opening extending therethrough, the balloon being inflatable to a volume of a person being treated, at least a portion of the balloon having a self-sealing substance to facilitate puncture thereof with insufflation means through which the balloon is inflated and to facilitate sealing of the puncture upon removal of the insufflation means.

2. A stomach insert as in claim 1 wherein the balloon has an inflated volume of approximately 200 to 800 cc.

3. A stomach insert as in claim 1 wherein the central opening in the balloon includes flared outer ends.

4. A method of treating obesity in humans comprising the steps of assembling a deflated stomach balloon with an insufflation tube releasably attached thereto inside a standard stomach tube, thereafter having a central opening extending therethrough introducing the stomach tube through the mouth and into the stomach, urging the balloon out of the stomach tube and into the stomach, inflating the balloon through the insufflation tube with a given amount of fluid to increase the volume thereof while enabling the inflated balloon to freely float within the stomach, and then removing the stomach tube and the insufflation tube from the stomach and out through the mouth whereby the inflated balloon is unattached and free to float within the stomach.

5. A method as in claim 4 wherein the balloon is inflated to a volume approximately 80% of the stomach volume.

6. A method as in claim 4 including the step of removing the balloon from the stomach by introducing extraction means through the mouth and into the stomach, grasping and puncturing the balloon with the extraction means, and then withdrawing the deflated balloon out of the stomach and through the mouth.

7. A method as in claim 6 wherein the extraction means includes a fiberoptic gastroscope with needle biopsy forceps.

* * * * *

UNITED STATES PATENT AND TRADEMARK OFFICE
CERTIFICATE OF CORRECTION

PATENT NO. : 4,416,267
DATED : November 22, 1983
INVENTOR(S) : Lloyd R. Garren; Mary L. Garren It is certified that error appears in the above-identified patent and that said Letters Patent is hereby corrected as shown below:

Column 1, line 62, "persons's" should be -- person's --

Column 4, claim 1, line 18, after "volume" should read

-- effective to reduce the stomach volume --

Column 4, claim 4, line 29, after "balloon" should read

-- having a central opening extending therethrough -- lines 31-32, after "thereafter" the phrase "having a central opening extending therethrough" should be deleted Signed and Sealed this Seventh Day of February 1984

[SEAL]

Attest:

GERALD J. MOSSINGHOFF

Attesting Officer

Commissioner of Patents and Trademarks